US006753456B2

(12) United States Patent
Lester et al.

(10) Patent No.: US 6,753,456 B2
(45) Date of Patent: Jun. 22, 2004

(54) POINT MUTANT MICE WITH HYPERSENSITIVE ALPHA 4 NICOTINIC RECEPTORS: DOPAMINERGIC PATHOLOGY AND INCREASED ANXIETY

(75) Inventors: Henry A. Lester, South Pasadena, CA (US); Cesar Labarca, Pasadena, CA (US); Johannes Schwarz, Leipzig (DE); Carlos Fonck, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 09/949,298

(22) Filed: Sep. 7, 2001

(65) Prior Publication Data

US 2002/0104107 A1 Aug. 1, 2002

Related U.S. Application Data

(60) Provisional application No. 60/230,757, filed on Sep. 7, 2000.

(51) Int. Cl.[7] ...................... G01N 33/00; A01K 67/027; C12N 15/00
(52) U.S. Cl. ................ 800/3; 800/18; 800/25
(58) Field of Search ............................... 800/3, 18, 25, 800/22

(56) References Cited

FOREIGN PATENT DOCUMENTS

WO   A-56247/96   1/1997
WO   00/26392   5/2000

OTHER PUBLICATIONS

Mullins and Mullins. Perspective Series: Molecular Medicine in Genetically Engineered Animals. Apr. 1, 1996. Clinical Investigation. vol. 97, No. 7, pp. 1557–1560.*
Sigmund. Viewpoint: Are Studies in Genetically Altered mice Out of Control? Jun., 2000. Arterioscler Thromb. Vasc. Biol. vol. 20. pp. 1425–1429.*
Wall. Transgenic Livestock: Progress and Prospects for the Future. 1996. Theriogenology. vol. 45, pp. 57–68.*
Ross et al. Phenotypic characterization of an alpha 4 neuronal nicotine acetylcholine receptor subunit knock out mouse. The Journal of Neuroscience, Sep. 1, 2000. vol. 20, No. 17, pp. 6431–6441.*

Campbell and Wilmut. Totipotency or Multipotentiality of Cultured Cells: Applications and Progress. Theriogenology. Jan. 1, 1997. vol. 47, No. 1, pp. 63–70.*
Jacks et al. Effects of an Rb mutation in the mouse. Sep. 24, 1992. Nature. vol. 359, pp. 295–300.*
Bradley et al. Modifying the Mouse: Design and Desire. May 1992. Biotechnology. vol. 10, pp. 534–539.*
Labarca et al., "Point mutant mice with hypersensitive α4 nicotinic receptors show dopaminergic deficits and increased anxiety," PNAS, vol. 98, No. 5, Feb. 27, 2001, pp. 2786–2791.
Labarca et al., "Knockin mice with hypersensitive neuronal nicotinic receptors," Society for Neuroscience Abstracts, vol. 26, No. 1–2 (2000).
Cordero–Erausquin et al., "Nicotinic receptor function: new perspectives from knockout mice," Elsevier Science Ltd., vol. 21, Jun. 2000, pp. 211–217.
Orr–Urtreger et al., "Mice Homozygous for the L250T Mutation in the α7 Nicotinic Acetylcholine Receptor Show Increased Neuronal Apoptosis and Die Within 1 Day of Birth," Jorunal of Neurochemistry, vol. 74, No. 5, 2000.
Marubio et al., "Reduced antinociception in mice lacking neuronal nicotinic receptor subunits," Nature, vol. 398, Apr. 29, 1999, pp 805–810.
Labarca et al., "Channel gating governed symmetrically by conserved leucine residues in the M2 domain of nicotinic receptors," Nature, vol. 376, Aug. 10, 1995.
Decker et al., "(S)–3–Methyl–5–(1–Methyl–2–Pyrrolidinyl)Isoxazole (ABT 418): A Novel Cholinergic Ligand with Cognition– Enhancing and Anxiolytic Activities: II. In Vivo Characterization," The Journal of Pharmacology and Experimental Therapeutics, vol. 270, No. 1, 1994, pp. 319–328.

* cited by examiner

Primary Examiner—Anne-Marie Falk
Assistant Examiner—Celine Qian
(74) Attorney, Agent, or Firm—Gray Cary Ware & Freidenrich, LLP

(57) ABSTRACT

The present invention relates to transgenic animals expressing a hypersensitive nicotinic acetylcholine receptor. Transgenic animals have point mutations in the nucleic acid sequence encoding the α4 subunit of the receptor that result in increased sensitivity to nicotine. Such transgenic animals are model systems for nicotine addiction and certain types of epilepsy.

11 Claims, 10 Drawing Sheets

Figure 1E
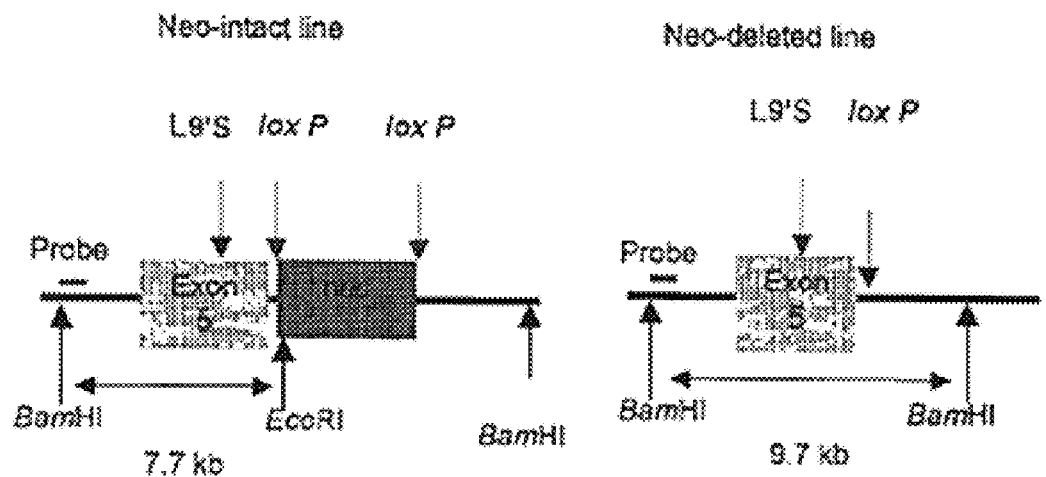
Figure 1F
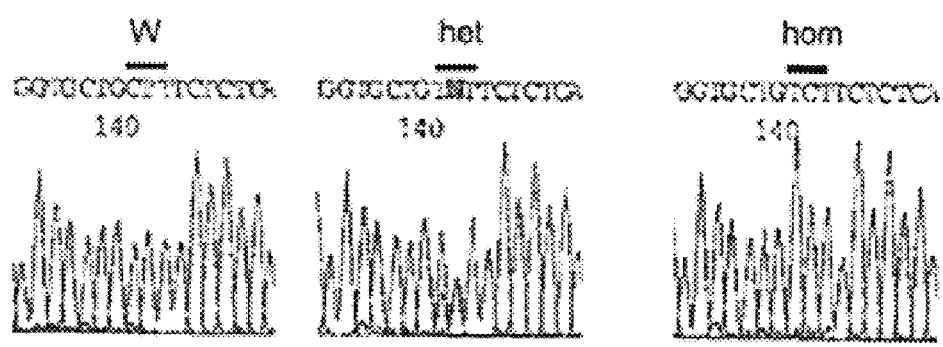
FIGURE 1E – 1F

Figure 2A
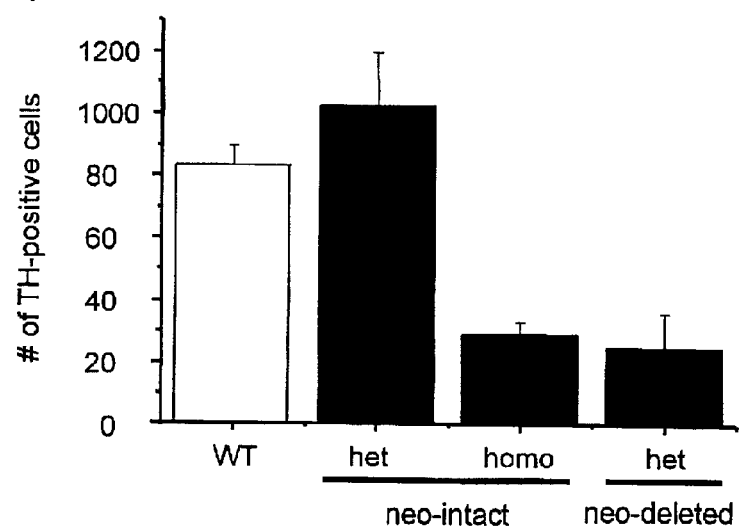
Figure 2B
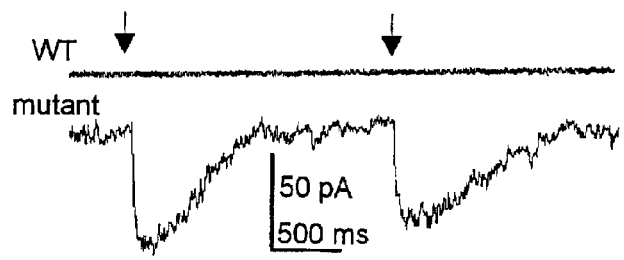
Figure 2C
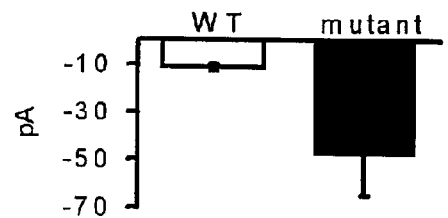
FIGURE 2A – 2C

Figure 3A
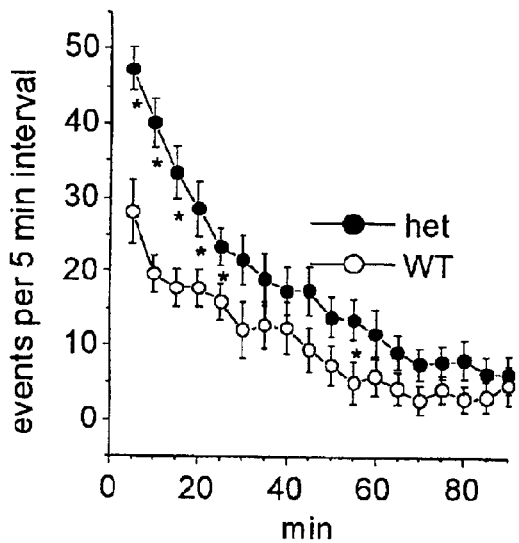
Figure 3B
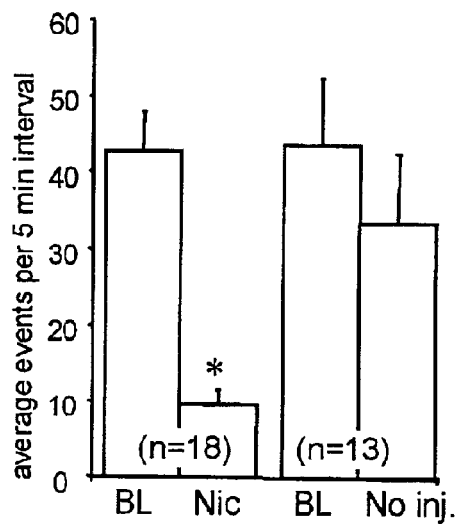
FIGURE 3A – 3B

Figure 3C
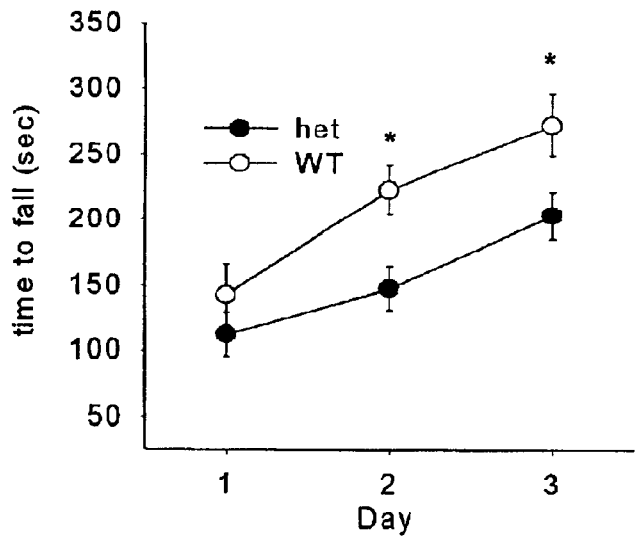
Figure 3D
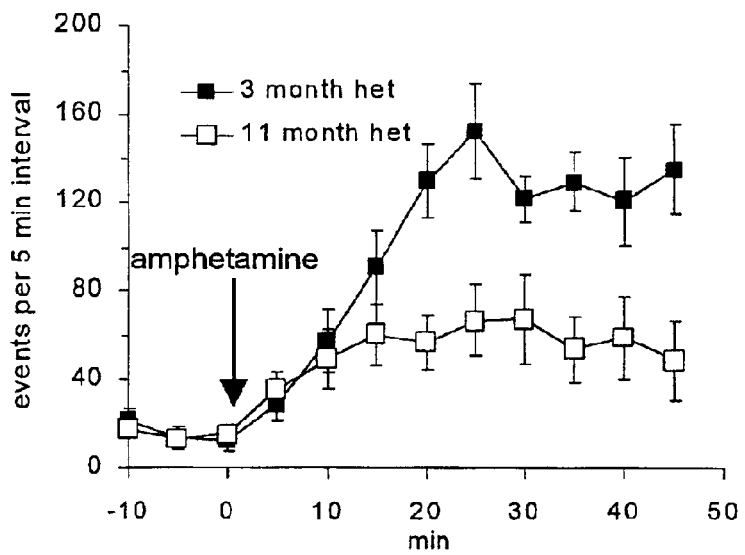
FIGURE 3C – 3D

Figure 4A
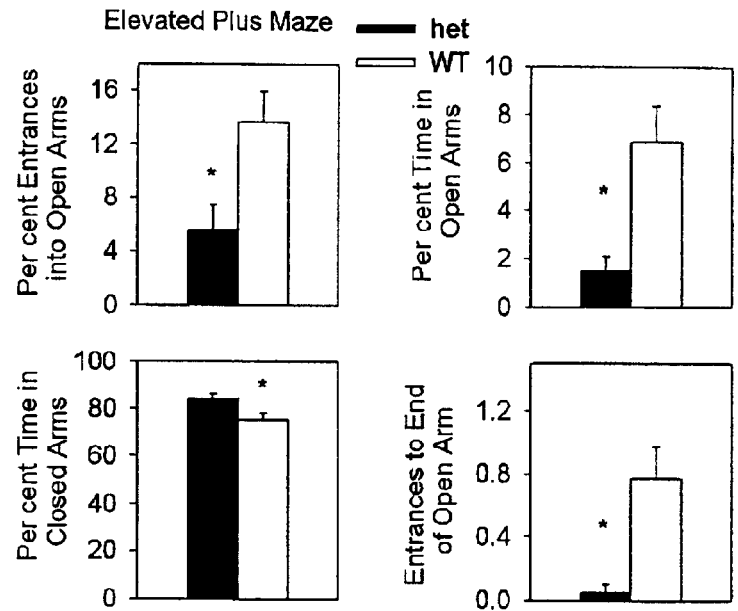
Figure 4B
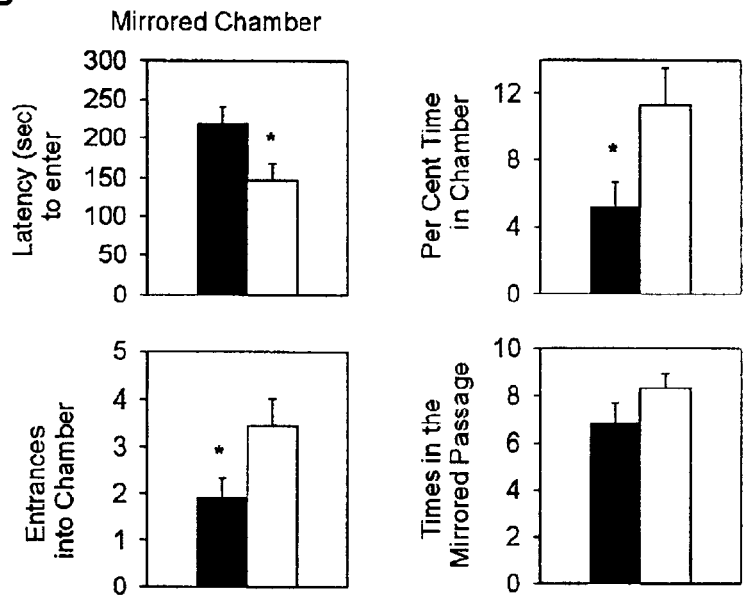
FIGURE 4A – 4B

SEQUENCE LISTING

<160> NUMBER OF SEQ ID NOS: 4

<210> SEQ ID NO 1
<211> LENGTH: 19
<212> TYPE: PRT
<213> ORGANISM: Mouse
<400> SEQUENCE: 1

```
Val Thr Leu Cys Ile Ser Val Leu Leu Ser Leu Thr Val Phe Leu Leu
1               5                   10                  15
Leu Ile Thr

<210> SEQ ID NO 2
<211> LENGTH: 17
<212> TYPE: DNA
<213> ORGANISM: Mouse
<400> SEQUENCE: 2
ggtgctgctt tctctca                                                  17

<210> SEQ ID NO 3
<211> LENGTH: 17
<212> TYPE: DNA
<213> ORGANISM: Mouse
<220> FEATURE:
<221> NAME/KEY: misc_feature
<222> LOCATION: (9)..(9)
<223> OTHER INFORMATION: n is any nucleotide
<400> SEQUENCE: 3
ggtgctgtnt tctctca                                                  17

<210> SEQ ID NO 4
<211> LENGTH: 17
<212> TYPE: DNA
<213> ORGANISM: Mouse
<400> SEQUENCE: 4
ggtgctgtct tctctca                                                  17
```

POINT MUTANT MICE WITH HYPERSENSITIVE ALPHA 4 NICOTINIC RECEPTORS: DOPAMINERGIC PATHOLOGY AND INCREASED ANXIETY

RELATED APPLICATIONS

This application claims the benefit of priority under 35 U.S.C. § 119 of Provisional Application Number 60/230,757, filed Sep. 7, 2000, incorporated herein in its entirety.

ACKNOWLEDGEMENT OF FEDERAL GOVERNMENT SUPPORT

This application was supported by Grant Numbers NS-11756, MH-49176, and DA11836, awarded by the National Institutes of Health. The Government may have certain rights in the invention.

FIELD OF INVENTION

The invention relates generally to animal model systems useful for examining and manipulating neurobehaviors mediated by nicotine. More specifically, the invention relates to knock-in mice having a leucine-to-serine mutation of the α4 nicotinic receptor subunit gene resulting in nicotine hypersensitivity, and to methods of using the knock-in mice to identify agents that modulate nicotine addiction and other neurobehaviors.

BACKGROUND OF THE INVENTION

The mechanism leading from nicotine intake to addiction begins with the activation of neuronal nicotinic acetylcholine receptors (nAChR). Nicotine elicits dopamine release in several regions of the brain, leading to reward, motor learning, and addictive effects. The highest-affinity and most abundant nicotine binding in the brain corresponds to a nAChR formed by α4 and $\mu$2 subunits. The α4 subunit is the principal partner for the β2 subunit in brain; β2-containing receptors play an important role in nicotine self-administration, in nicotine-stimulated electrophysiological responses in midbrain neurons, and in nicotine-stimulated dopamine release in the ventral striatum. The α4 subunit is localized in dopaminergic neurons with tyrosine hydroxylase. The α4 and β2 subunits are also the site of at least five point mutations that cause the human disease, autosomal dominant nocturnal frontal lobe epilepsy (ADNFLE).

Nicotine is known to reduce anxiety, or to produce a bimodal effect on anxiety. Nicotinic receptors modulate the release of neurotransmitters, for example γ-aminobutyric acid, dopamine, and serotonin, that have critical roles in the regulation of anxiety. The mechanism by which nicotine reduces anxiety is not well understood, but results from several studies suggest that nicotine-mediated effects on neurons in which nicotine is a co-transmitter may play important roles. Accordingly, a model system for studying nicotinic neurotransmission and the role of the nicotinic acetylcholine receptor is of key importance.

BRIEF DESCRIPTION OF INVENTION

In one embodiment of the invention there is provided a transgenic non-human animal having a transgene comprising a leucine-to-serine mutation of the α4 nicotinic receptor subunit chromosomally integrated into germ cells of the animal. The leucine to serine mutation is located in the M2 transmembrane region of the acetylcholine receptor.

In another embodiment of the invention there is provided a transgenic mouse comprising a transgene having a leucine-to-serine mutation at 9' of the α4 nicotinic receptor subunit. Expression of the receptor subunit gene results in a mouse that displays modified behavior compared to a normal mouse. The transgenic mouse displays nicotinic hypersensitivity, increased anxiety, increased sensitivity to seizures, poor motor learning, excessive ambulation, a reduction in dopaminergic neuron function upon aging, or any combination thereof.

In another embodiment of the invention there is provided a transgenic mouse comprising a transgene having a single codon change in the α4 nicotinic receptor subunit. Expression of the receptor subunit gene results in a mouse that displays modified behavior compared to a normal mouse. The transgenic mouse displays nicotinic hypersensitivity, increased anxiety, increased sensitivity to seizures, poor motor learning, excessive ambulation, a reduction in dopaminergic neuron function upon aging, susceptibility to seizure, spontaneous seizures, or any combination thereof.

In yet another embodiment of the invention there is provided a method for screening a candidate agent for the ability to modulate nicotine-mediated behavior in a transgenic animal. The method includes administering to a first transgenic animal a candidate agent and comparing nicotine-mediated behavior in the animal to the nicotine-mediated behavior of a second transgenic animal not administered the candidate agent. A difference in nicotine-mediated behavior in the animal administered the candidate agent compared to the animal not administered the agent is indicative of an agent that modifies nicotine-mediated behavior.

In still another embodiment of the invention there is provided a method for screening for candidate agents that modulate nicotine hypersensitivity. The method includes administering a candidate agent to a transgenic animal and determining the effect of the agent upon a cellular or molecular process associated with nicotinic hypersensitivity compared to an effect of the agent administered to a non-transgenic animal.

In another embodiment, there is provided a method for screening for candidate agents that modulate seizures associated with epilepsy. The method includes administering a candidate agent to a transgenic animal and determining the effect of the agent upon seizure activity associated with epilepsy compared to an effect of the agent administered to a non-transgenic animal.

BRIEF DESCRIPTION OF FIGURES

In FIG. 1A, the agonist is acetylcholine; in

FIG. 1B, the agonist is nicotine and in

FIG. 1C, the agonist is choline. The choline responses of the WT receptor were not studied systematically, because there is no response at choline concentrations up to 1 mM, and higher concentrations of choline block the channel. FIG. 1C insert shows the time course of the response to 30 $\mu$M choline, showing partial desensitization.

FIG. 1E shows that deletion of the neo cassette by transfecting the neo-intact ES cells with a cytomegalovirus-Cre plasmid generates neo-deleted ES cell lines.

FIG. 1F shows sequence analysis of DNA extracted from WT (SEQ ID NO:2) heterozygous (het: SEQ ID NO:3), and homozygous (hom: SEQ ID NO:5) neo-intact mice. The WT sequence at nucleotide position 142, corresponding to the codon at position 9' in the M2 region, is CTT, encoding leucine; the mutant sequence is TCT, encoding serine.

FIG. 2A shows cell counts of tyrosine hydroxylase (TH)-positive neurons in substantia nigra of ED 16 to ED 18 embryos from WT, neo-intact, and neo-deleted mice. The heterozygote (het) cell counts do not differ significantly from WT, but both the homozygous (homo) neo-intact (P, 0.01, f test) and the neo-deleted cell counts (P, 0.05, t test) differ significantly from WT.

FIG. 2B shows whole-cell voltage-clamp recording of responses to two consecutive puffs of choline (100 μM, 20 ms) in neuron-like cells differentiated from ED 16 midbrain neuronal progenitor cells. Upper trace, cell from a WT embryo; lower trace, cell derived from a heterozygous neo-intact ED 16 embryo.

FIG. 2C shows the mean ±SEM of responses in neuron-like cells derived from heterozygous animals (n=5 cells) but little or no response in cells from WT animals (n=7 cells; significant difference, P, 0.05, t test).

FIG. 3 shows spontaneous and drug-modulated locomotion of WT and heterozygous (het) neo-intact mutants.

FIG. 3A shows the effect of no treatment. Heterozygotes showed significantly higher locomotion than WT mice at the beginning of the experiment (P, 0.001).

FIG. 3B shows locomotion after nicotine, 0.02 mg/kg, was injected 30 min after the start of behavioral monitoring. The plot shows data averaged over the time periods, 10 min before baseline (BL) and 5–15 min after injection. Heterozygous mice showed a significant reduction of locomotor activity after nicotine injection (P, 0.05). There was no significant difference in non-injected animals (right-hand bars), nicotine-injected control animals, or saline-injected WT or heterozygous animals.

FIG. 3C shows that heterozygotes were impaired compared with WTs on the accelerating rotarod (P, 0.012) when tested for three sequential days (n=20–22 of each genotype).

FIGS. 3D and 3E show the effect of amphetamine on locomotion of WT and heterozygous (het) mice at two ages. Before drug administration, animals were allowed to habituate for 30 min. Ten male WT and 10 male heterozygous mice showing at least a three-fold increased activity over baseline in response to amphetamine at three months of age were selected for longitudinal follow-up studies.

FIG. 3D shows a comparison in amphetamine responses for heterozygotes at 3 months vs. 11 months of age.

FIG. 3E shows the average activity plotted for the period between 5 and 45 min after injection. The response at 11 months declines significantly compared with the response at three months in heterozygous mice [F(1,9)=12.72, P, 0.01] but not in WT mice.

FIG. 4 shows the increased anxiety in α4 heterozygotes (het) compared with WT mice in the elevated plus maze (A) and mirrored chamber (B)(n=22 mice of each genotype).

FIG. 4A shows that heterozygotes were significantly more anxious, as measured by percentage of entrances into the open arms (P, 0.01), percentage of time in the open arms (P, 0.002), percentage of time in the closed arms (P, 0.02), and entrances to the end of the open arms (P, 0.005).

FIG. 4B shows that heterozygotes were significantly more anxious in the mirrored chamber, as measured by latency to enter the mirrored chamber (P, 0.026), percentage of time in the mirrored chamber (P, 0.03), entrances into the mirrored chamber (P, 0.02), but not by the number of entries into the mirrored passage.

FIG. 5A shows seizure scores and

FIG. 5B shows Straub tail scores. The means of six animals ±1 SE are shown.

DETAILED DESCRIPTION OF INVENTION

Figure 1:
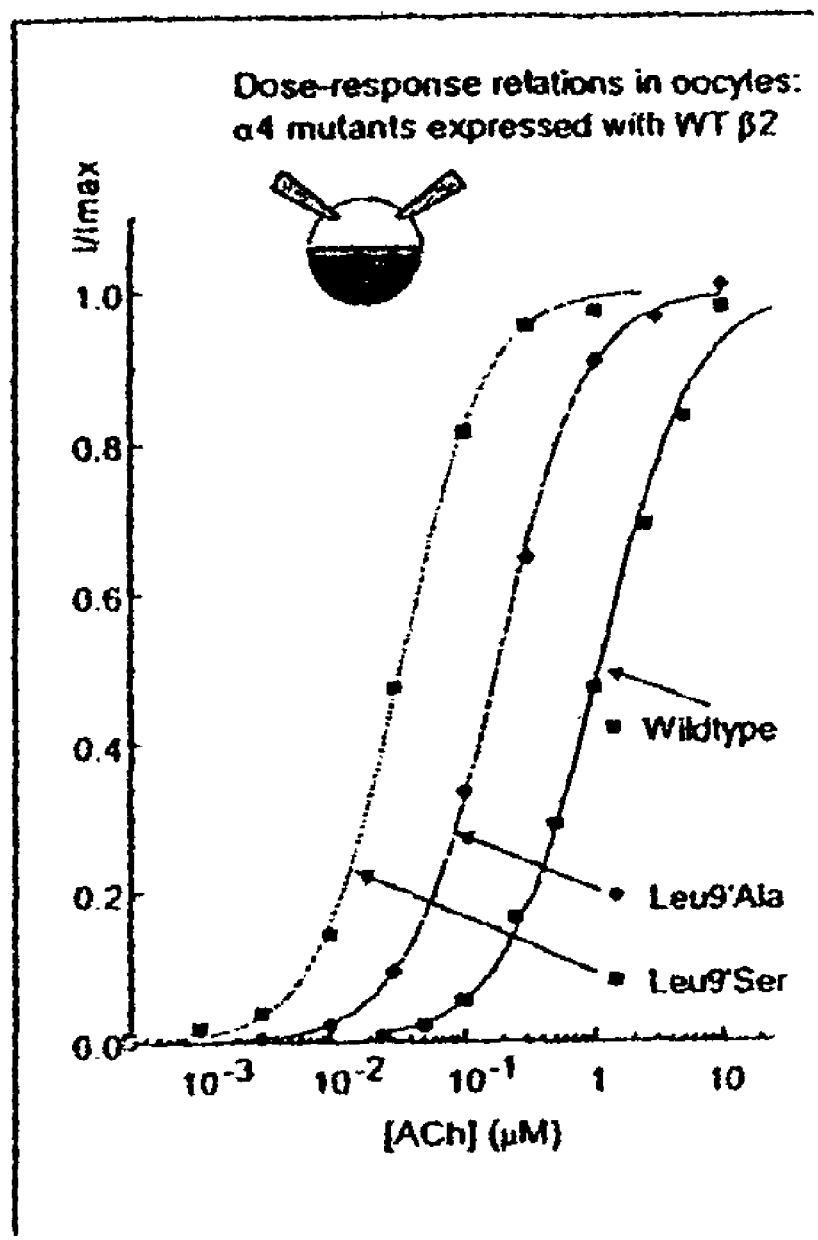
FIG. 1 shows the physiological design, recombinant construction, and genomic characterization of the α4 knock-in mouse strains.

The present invention relates to transgenic animals expressing a hypersensitive nicotinic acetylcholine receptor. Nicotinic acetylcholine receptors, multi-subunit proteins, are members of a ligand-gated receptor family and mediate rapid synaptic transmission in the central and peripheral nervous systems. The highest affinity and most abundant nicotine binding in the brain corresponds to a nicotinic acetylcholine receptor formed by α4 and β2 subunits. The α4 subunit is the principal partner for the β2 subunit in the brain. Transgenic mice that are deficient in either the α4 or β2 subunit, i.e., "knockout mice" show only subtle alterations in their physiology or behavior until they reach old age.

The present invention provides transgenic mice that are hypersensitive in receptor function. "Knock-in" mice are generated by introducing a point mutation in the α4 subunit. Such phenotypes are especially useful since nicotine and some candidate analgesics are agonists of the nicotinic acetylcholine receptor. In addition, such phenotypes are useful because autosomal dominant nocturnal frontal lobe epilepsy (ADNFLB) can result from gain-of function (that is, hypersensitive) point mutations in the α4 subunit of the nicotinic acetylcholine receptor.

As used herein, a "transgene" used in the practice of the invention is a DNA sequence comprising a modified α4 receptor subunit sequence. The gene construct contains a leucine to serine mutation in transmembrane region M2 at 9'. The mutation is at nucleotide position 142 resulting in wild type codon CTT encoding leucine being mutated to TCT, encoding serine. The mutated receptor contains a point mutation having serine in place of leucine at 9'. Where appropriate, DNA sequences that encode proteins having the same amino acid mutation but differ in nucleic acid sequence due to the degeneracy of the genetic code may also be used herein. For example, serine is encoded by each of the following codons: TCT, TCC, TCA, TCG, AGU and AGC. In addition, sequences having truncated forms, allelic variants and interspecies homologues can also be used.

The expression of the transgene in an animal creates a "knock-in" animal. As used herein, a "knock-in" animal has a leucine-to serine mutation at the 9' position in the M2 region of the α4 nicotinic receptor. Mice with intact homozygous expression of the leucine-to-serine α4 mutant receptor subunit display dominant neonatal lethality. Mice that are heterozygous for the transgene are viable and fertile, and a breeding colony can be established. Transgenic heterozygous mice contain, in addition to the mutant α4 nicotinic receptor, a neomycin resistance cassette with a phosphoglycerate kinase promoter and polyadenylation signal and flanked by loxP sites. The neomycin resistance cassette, "neo" may be wholly or partially deleted during transfection. Such deletion during the transfection process can result in transgenic mice with the neo cassette still present (neo intact) and with the neo cassette deleted (neo deleted).

Heterozygous animals from the neo-deleted line do not feed and die within 24 hours after birth. Heterozygous animals from the neo intact line are viable and these animals are referred to herein as "heterozygous". Neo intact homozygous animals do not feed and die within the first postnatal day. (See Example 1).

In some embodiments of the invention, a knock-in animal displaying nicotine hypersensitivity, increased susceptibility to seizures, spontaneous seizures, increased ambulation, poor motor learning, increased anxiety, a reduction in dopaminergic neuron function upon aging, or any combination thereof has a point mutation in the nucleotide encoding leucine at the 9' position in the M2 region of the α4 nicotinic receptor subunit such that in the protein sequence of the subunit, leucine is replaced by another amino acid. Preferably leucine is replaced by threonine. Leucine can also be replaced by glycine, alanine, valine, or iosleucine, or by alanine or proline, or by phenylalanine, tyrosine, tryptophan, or by lysine, arginine or histidine, or by aspartate, glutamate, asparagine, glutamine, cysteine or methoione.

Knock-in animals of the invention display alterations in their behavior and anatomical and, physiological process. The nervous system of knock in mice shows such anatomical processes as a severe deficit of dopaminergic neurons in the substantia nigra compared to wild type animals. Behavioral changes also characterize knock-in mice. Transgenic mice display increased ambulation, increased anxiety and poor motor learning compared to wild type mice. The knock in mice also display increased sensitivity to nicotine, i.e., nicotine hypersensitivity. (See Examples 3 and 4.)

Knock in mice of the invention, also display susceptibility to seizure and spontaneous seizure. Seizure, and recurrent seizures, consisting of synchronous and rhythmic firing of neuronal populations characterize the brain disorder epilepsy. Recurrent seizures can occur sporadically or randomly, with no apparent triggering, i.e., spontaneously. The hallmark of the altered physiologic state of epilepsy is a rhythmic and repetitive hypersynchronous discharge of many neurons in a localized area of the brain. In an epileptic focus, neurons in a small area of the cortex are activated for a brief period (50 to 100 ms) in an unusually synchronized manner and are then inhibited. If the synchronous neuronal discharge occurs repetitively over several seconds, a focal seizure follows; if it spreads through the brain and lasts for many seconds or minutes, a complex partial or generalized seizure will occur. Any physiological event that makes it more likely that the initial activation occurs, or that allows the neuronal discharge to occur repetitively, or that allows the focal seizure to spread through the brain and last for many seconds increases susceptibility to seizure (see *Harrison's Principles of internal Medicine*, eds. Isselbacher et al. McGraw Hill, N.Y., 13$^{th}$ edition, 1994).

It has been difficult to identify the molecular and cellular events responsible for epilepsy, in part because there are a disparate multitude of epileptic syndromes classified according to symptoms, response to medication, age of onset, neuroanatomical substrate and electroencephalographic patterns. In general, it is thought that epileptic seizures are the result of an unbalance between excitatory and inhibitory forces governing neurons, that favors excitation to the point of seizure induction (see McNamara, J. O. (1999) *Nature* 399, A15–22, for review and Example 4.)

Of the several dozen phenotypic epileptic characters that are recognized as signs of Mendelian inheritance, only a few genes have been causally linked to specific epileptic disorders. In particular, ADNFLE is one of the rare epileptic syndromes caused by point mutations, and the first such epilepsy identified that involves ligand gated receptor channel subunits, namely, the α4 and β2 subunits of the nAChRs. Due to its single-gene inheritance, and because of advances in our knowledge in molecular biology and receptor channel physiology, ADNFLE provides an excellent opportunity to devise experimental approaches to study epilepsy. The ADNFLE point mutations in the M2 segment of the α4 subunit, which is the putative pore-lining region of nAChRs, are α4(S248F) (Steinlein, et al. (1995). Nat Genet 11, 201–3), α4(777ins3) (Steinlein, et al. (1997) Hum Mol Genet 6, 943–7), and α4(S252L) (Hirose, et al. (1999). *Neurology* 53, 1749–53). More recently, two missense mutations have been identified in the same locus of the M2 region of the β2 subunit of nAChRs: V287L (De Fusco, et al. (2000) *Nat Genet* 26, 275–6) and V287M (Phillips, et al. (2001). *Am J Hum Genet* 68, 225–31). Occurrence of ADNFLE mutations in the M2 pore-forming region of both α4 and β2 subunits, should not be regarded as mere coincidence, since these two subunits combine to form the predominant nAChR subtype in the brain (Whiting and Lindstrom (1988). *J Neurosci* 8, 3395–404; and Flores, et al. (1992) *Mol. Pharmacol.* 41, 31–37). Similar clinical symptoms, that is, frequent, brief and sometimes violent seizures, starting during childhood, originating in frontal cortex and occurring during sleep, are shared by the five ADNFLE alleles isolated from five different families in Europe and Australia. The fact that all these mutations in the M2 regions of nAChR subunits cause ADNFLE, suggests that several changes in the α4β2 receptor pore-forming region may render this specific epileptic phenotype.

Also included when animals are referred to as transgenic are "knockout animals". For purposes of the subject invention, these animals have been manipulated so that there is disruption or interference with the activity or expression of a gene, i.e., α4 nicotinic receptor subunit. As used herein, disruption or interference with the activity or expression refers to a manipulation such that the transgenic animal is irreversibly defective for all or essentially all of an activity of one or more specific gene/allele product(s) relative to the corresponding wild type animal. As used herein the term "knockout animal" can therefore include the heterozygote animal (e.g., one defective allele and one wild-type allele), a homozygous animal (e.g., two defective alleles) or an animal having more than one gene having at least allele that has been inactivated. A knockout animal that is heterozygous for a particular gene product activity has been manipulated to be defective for all or "essentially all" of the activity of at least one of the particular allele products relative to the corresponding wild type animal.

As used herein, a knockout animal or cell defective for "essentially all" of an activity of a specific gene/allele product, is an animal or cell that has less than about 25% of the gene/allele product activity of the corresponding wild type animal or wild type cell. In certain embodiments, the animal or cell has less than or equal to about 20% of the gene/allele product activity of the corresponding wild type animal or wild type cell respectively.

Also provided by the invention is a transgenic mouse comprising a disruption in α4 nicotinic acetylcholine receptor (α4 nAChR) gene, wherein the disruption of the α4 nAChR gene results in a mouse that produces no or low detectable levels of α4 nAChR. α4 nAChR levels can be detected by methods known to those of skill in the art. For example, Western blotting using antibodies that specifically recognize α4 nAChR can be used to assess the relative level of α4 nAChR in tissue samples (see Examples). Antibodies against α4 nAChR can also be used in immunocytochemical methods to assess the presence of α4 nAChR in tissue sections). Such antibodies can also be used in antibody-based assays such as radioimmune assays and enzyme-linked immunoabsorbant assays (ELISA) to determine the level of α4 nAChR.

A "transgenic" animal can be produced by cross-breeding two chimeric animals which include exogenous genetic material within cells used in reproduction. Twenty-five percent of the resulting offspring will be transgenic, i.e., animals that include the exogenous genetic material within all of their cells in both alleles. Fifty percent of the resulting animals will include the exogenous genetic material within one allele and twenty five percent will include no exogenous genetic material.

Various methods to make the transgenic animals of the subject invention can be employed. Generally speaking, three such methods may be employed. In one such method, an embryo at the pronuclear stage (a "one cell embryo") is harvested from a female and the transgene is microinjected into the embryo, in which case the transgene will be chromosomally integrated into both the germ cells and somatic cells of the resulting mature animal.

In another method, embryonic stem cells are isolated and the transgene incorporated therein by electroporation, plasmid transfection or microinjection, followed by reintroduction of the stem cells into the embryo where they colonize and contribute to the germ line. Methods for microinjection of mammalian species is described in U.S. Pat. No. 4,873,191.

In yet another such method, embryonic cells are infected with a retrovirus containing the transgene whereby the germ cells of the embryo have the transgene chromosomally integrated therein. When the animals to be made transgenic are avian, because avian fertilized ova generally go through cell division for the first twenty hours in the oviduct, microinjection into the pronucleus of the fertilized egg is problematic due to the inaccessibility of the pronucleus. Therefore, of the methods to make transgenic animals described generally above, retrovirus infection is preferred for avian species, for example as described in U.S. Pat. No. 5,162,215. If microinjection is to be used with avian species, however, a recently published procedure by Love et al., (Biotechnology, 12, Jan 1994) can be utilized whereby the embryo is obtained from a sacrificed hen approximately two and one-half hours after the laying of the previous laid egg, the transgene is microinjected into the cytoplasm of the germinal disc and the embryo is cultured in a host shell until maturity. When the animals to be made transgenic are bovine or porcine, microinjection can be hampered by the opacity of the ova thereby making the nuclei difficult to identify by traditional differential interference-contrast microscopy. To overcome this problem, the ova can first be centrifuged to segregate the pronuclei for better visualization.

The "non-human animals" of the invention include murine, bovine, porcine, ovine, piscine and avian animals (e.g., mouse, cow, pig, fish, sheep, chicken, turkey). The "transgenic non-human animals" of the invention are produced by introducing "transgenes" into the germline of the non-human animal. Embryonal target cells at various developmental stages can be used to introduce transgenes. Different methods are used depending on the stage of development of the embryonal target cell. The zygote is the best target for microinjection. The use of zygotes as a target for gene transfer has a major advantage in that in most cases the injected DNA will be a=incorporated into the host gene before the first cleavage (Brinster et al., *Proc. Natl. Acad Sci. USA* 82:4438–4442, 1985). As a consequence, all cells of the transgenic non-human animal will carry the incorporated transgene. This will in general also be reflected in the efficient transmission of the transgene to offspring of the founder since 50% of the germ cells will harbor the transgene.

In the microinjection method useful in the practice of the subject invention, the transgene is digested and purified free from any vector DNA e.g. by gel electrophoresis. It is preferred that the transgene include an operatively associated promoter which interacts with cellular proteins involved in transcription, ultimately resulting in constitutive expression. Promoters useful in this regard include those from cytomegalovirus (CMV), Moloney leukemia virus (MLV), and herpes virus, as well as those from the genes encoding metallothionin, skeletal actin, P-enolpyruvate carboxylase (PEPCK), phosphoglycerate (PGK), DHFR, and thymidine kinase. Promoters for viral long terminal repeats (LTRs) such as Rous Sarcoma Virus can also be employed. When the animals to be made transgenic are avian, preferred promoters include those for the chicken γ-globin gene, chicken lysozyme gene, and avian leukosis virus. Constructs useful in plasmid transfection of embryonic stem cells will employ additional regulatory elements well known in the art such as enhancer elements to stimulate transcription, splice acceptors, termination and polyadenylation signals, and ribosome binding sites to permit translation.

Retroviral infection can also be used to introduce transgene into a non-human animal, as described above. The developing non-human embryo can be cultured in vitro to the blastocyst stage. During this time, the blastomeres can be targets for retro viral infection (Jaenich, R., Proc. Natl. Acad. Sci USA 73:1260–1264, 1976). Efficient infection of the blastomeres is obtained by enzymatic treatment to remove the zona pellucida (Hogan, et al. (1986) in Manipulating the Mouse Embryo, Cold Spring Harbor Laboratory Press, Cold Spring Harbor, N.Y.). The viral vector system used to introduce the transgene is typically a replication-defective retro virus carrying the transgene (Jahner, et al., *Proc. Natl. Acad. Sci. USA* 82:6927–6931, 1985; Van der Putten, et al., *Proc. Natl. Acad Sci USA* 82:6148–6152, 1985). Transfection is easily and efficiently obtained by culturing the blastomeres on a monolayer of virus-producing cells (Van der Putten, supra; Stewart, et al., *EMBO J.* 6:383–388, 1987). Alternatively, infection can be performed at a later stage. Virus or virus-producing cells can be injected into the blastocoele (D. Jahner et al., *Nature* 298:623–628, 1982). Most of the founders will be mosaic for the transgene since incorporation occurs only in a subset of the cells which formed the transgenic nonhuman animal. Further, the founder may contain various retro viral insertions of the transgene at different positions in the genome which generally will segregate in the offspring. In addition, it is also possible to introduce transgenes into the germ line, albeit with low efficiency, by intrauterine retroviral infection of the midgestation embryo (D. Jahner et al., supra).

A third type of target cell for transgene introduction is the embryonal stem cell (ES). ES cells are obtained from pre-implantation embryos cultured in vitro and fused with embryos (M. J. Evans et al. *Nature* 292:154–156, 1981; M. O. Bradley et al., *Nature* 309: 255–258, 1984; Gossler, et al., *Proc. Natl. Acad. Sci USA* 83: 9065–9069, 1986; and Robertson et al., *Nature* 322:445–448, 1986). Transgenes can be efficiently introduced into the ES cells by DNA transfection or by retro virus-mediated transduction. Such transformed ES cells can thereafter be combined with blastocysts from a nonhuman animal. The ES cells thereafter colonize the embryo and contribute to the germ line of the resulting chimeric animal. (For review see Jaenisch, R., *Science* 240: 1468–1474, 1988).

"Transformed" means a cell into which (or into an ancestor of which) has been introduced, by means of recombinant nucleic acid techniques, a heterologous nucleic acid molecule. "Heterologous" refers to a nucleic acid sequence that either originates from another species or is modified from either its original form or the form primarily expressed in the cell.

"Transgene" means any piece of DNA which is inserted by artifice into a cell, and becomes part of the genome of the organism (i.e., either stably integrated or as a stable extra-chromosomal element) which develops from that cell. Such a transgene may include a gene which is partly or entirely heterologous (i.e., foreign) to the transgenic organism, or may represent a gene homologous to an endogenous gene of the organism. Included within this definition is a transgene created by the providing of an RNA sequence which is transcribed into DNA and then incorporated into the genome. The transgenes of the invention include DNA sequences that include antisense, dominant negative encoding polynucleotides, which may be expressed in a transgenic non-human animal. The term "transgenic" as used herein additionally includes any organism whose genome has been altered by in vitro manipulation of the early embryo or fertilized egg or by any transgenic technology to induce a specific gene knockout. The term "gene knockout" as used herein, refers to the targeted disruption of a gene in vivo with complete loss of function that has been achieved by any transgenic technology familiar to those in the art. In one embodiment, transgenic animals having gene knockouts are those in which the target gene has been rendered nonfunctional by an insertion targeted to the gene to be rendered non-functional by homologous recombination. As used herein, the term "transgenic" includes any transgenic technology familiar to those in the art which can produce an organism carrying an introduced transgene or one in which an endogenous gene has been rendered non-functional or "knocked out."

An example of a transgene used to "knock-in" α4 nAChR function in the present Examples is described in Example 1 and see FIG. 1. Thus, in another embodiment, the invention provides a transgene wherein the α4 genomic clone contains a Leu9'Ser mutation. The α4 genomic clone can also contain part or all of exon 5. (See Example 1).

After an embryo has been microinjected, colonized with transfected embryonic stem cells or infected with a retrovirus containing the transgene (except for practice of the subject invention in avian species which is addressed elsewhere herein) the embryo is implanted into the oviduct of a pseudopregnant female. The consequent progeny are tested for incorporation of the transgene by Southern blot analysis of blood samples using transgene specific probes. PCR is particularly useful in this regard. Positive progeny (G0) are crossbred to produce offspring (G1) which are analyzed for transgene expression by Northern blot analysis of tissue samples. To be able to distinguish expression of like-species transgenes from expression of the animals' endogenous α4 nAChR gene(s), a marker gene fragment can be included in the construct in the 3' untranslated region of the transgene and the Northern probe designed to probe for the marker gene fragment. The levels of mutant α4 nAChR can also be measured in the transgenic animal to establish appropriate expression.

The expression of transgenes can also be assessed by the incorporation of reporter molecules. Reporter molecules, which confer a detectable phenotype on a cell, are well known in the art and include, for example, fluorescent polypeptides such as green fluorescent protein, cyan fluorescent protein, red fluorescent protein, or enhanced forms thereof, an antibiotic resistance polypeptide such as puromycin N-acetyltransferase, hygromycin B phosphotransferase, neomycin (aminoglycoside) phosphotransferase, and the Sh ble gene product; a cell surface protein marker such as the cell surface protein marker neural cell adhesion molecule (N-CAM); an enzyme such as beta-lactamase, chloramphenicol acetyltransferase, adenosine deaminase, aminoglycoside phosphotransferase, dihydrofolate reductase, thymidine kinase, luciferase or xanthine guanine phosphoribosyltransferase polypeptide; or a peptide tag such as a c-myc peptide, a polyhistidine, a FLAG epitope, or any ligand (or cognate receptor), including any peptide epitope (or antibody, or antigen binding fragment thereof, that specifically binds the epitope; see, for example, Hopp et al., *BioTechnology* 6:1204 (1988); U.S. Pat. No. 5,011,912, each of which is incorporated herein by reference). Expression of a reporter molecule can be detected using the appropriate instrumentation or reagent, for example, by detecting fluorescence of a green fluorescent protein or light emission upon addition of luciferin to a luciferase reporter molecule, or by detecting binding of nickel ion to a polypeptide containing a polyhistidine tag. Similarly, expression of a selectable marker such as an antibiotic can be detected by identifying the presence of cells growing under the selective conditions.

A reporter molecule also can provide a means of isolating or selecting a cell expressing the reporter molecule. For example, the reporter molecule can be a polypeptide that is expressed on a cell surface and that contains an operatively linked c-myc epitope; an anti-c-myc epitope antibody can be immobilized on a solid matrix; and cells, some of which express the tagged polypeptide, can be contacted with the matrix under conditions that allow selective binding of the antibody to the epitope. Unbound cells can be removed by washing the matrix, and bound cells, which express the reporter molecule, can be eluted and collected. Methods for detecting such reporter molecules and for isolating the molecules, or cells expressing the molecules, are well known to those in the art (see, for example, Hopp et al., supra, 1988; U.S. Pat. No. 5,011,912). As indicated above, a convenient means of isolating and selecting cells expressing a reporter molecule is provided by using a reporter molecule that confers antibiotic resistance, and isolating cells that grow in the presence of the particular antibiotic, e.g., neomycin.

Also provided by the invention is a method for screening a candidate agent for the ability to modulate nicotine-mediated behavior a transgenic animal that has a transgene comprising a leucine to serine mutation of the α4 nicotinic receptor subunit chromosomally integrated into germ cells of the animal. The method includes introducing a transgene comprising a selectable marker sequence into a mouse embryonic stem cell and introducing the stem cell into a mouse embryo. The embryo is transplanted into a pseudopregnant mouse and the embryo is allowed to develop to term when a transgenic mouse whose genome comprises a leucine to serine mutation of the α4 nicotinic receptor subunit gene is identified.

As used herein, "non-transgenic mouse" and "normal mouse" refers to a wild-type mouse or a mouse in which the nucleic acid sequence, activity or expression of the α4 nicotinic acetylcholine receptor gene has not been manipulated. In such a non-transgenic mouse, the α4 nAChR level would be expected to be within a normal range and a normal, i.e., non-mutant, form of α4 nAChR is expressed. A non-mutant α4 nAChR has a normal sensitivity to stimulation by nicotine. As used herein, the term "wild type," when used in reference to an animal, for example, a wild type mouse, refers to the animal as it exists in nature.

Also provided by the invention is a method for screening a candidate agent for the ability to modulate nicotine-mediated behavior in a transgenic animal. The method includes administering to a first transgenic animal a candidate agent and comparing nicotine-mediated behavior of the first transgenic animal to the nicotine-mediated behavior of a second transgenic animal not administered the candidate agent. A difference in nicotine-mediated behavior in the first transgenic animal administered the candidate agent compared to the second transgenic animal not administered the candidate agent is indicative of a candidate agent that modifies nicotine-mediated behavior.

Nicotine-mediated behavior includes anxiety. A candidate agent having the ability to modulate nicotine-mediated behavior can decrease anxiety. Nicotine-mediated behavior also includes ambulation; a candidate agent having the ability to modulate nicotine-mediated behavior can decrease ambulation. Yet another nicotine-mediated behavior is motor learning; a candidate agent having the ability to modulate nicotine-mediated behavior can improve motor learning. Nicotine-mediated behaviors can be assessed by methods known to those of skill in the art and including described in Examples 3.

The term "candidate agent" is used herein to mean any agent that is being examined for ability to modulate nicotine-mediated activity in a method of the invention. Although the method generally is used as a screening assay to identify previously unknown molecules that can act as a therapeutic agent, a method of the invention also can be used to confirm that an agent known to have such activity, in fact has the activity, for example, in standardizing the activity of the therapeutic agent.

A candidate agent can be any type of molecule, including, for example, a peptide, a peptidomimetic, a polynucleotide, or a small organic molecule, that one wishes to examine for the ability to act as a therapeutic agent, which is an agent that provides a therapeutic advantage to a subject receiving it. It will be recognized that a method of the invention is readily adaptable to a high throughput format and, therefore, the method is convenient for screening a plurality of test agents either serially or in parallel. The plurality of test agents can be, for example, a library of test agents produced by a combinatorial method library of test agents. Methods for preparing a combinatorial library of molecules that can be tested for therapeutic activity are well known in the art and include, for example, methods of making a phage display library of peptides, which can be constrained peptides (see, for example, U.S. Pat. Nos. 5,622,699; 5,206,347; Scott and Smith, *Science* 249:386–390, 1992; Markland et al., *Gene* 109:1319, 1991; each of which is incorporated herein by reference); a peptide library (U.S. Pat. No. 5,264,563, which is incorporated herein by reference); a peptidomimetic library (Blondelle et al., *Trends Anal. Chem.* 14:8392, 1995; a nucleic acid library (O'Connell et al., supra, 1996; Tuerk and Gold, supra, 1990; Gold et al., slpra, 1995; each of which is incorporated herein by reference); an oligosaccharide library (York et al., *Carb. Res.*, 285:99128, 1996; Liang et al., *Science,* 274:1520–1522, 1996; Ding et al., *Adv. Expt. Med. Biol.,* 376:261–269, 1995; each of which is incorporated herein by reference); a lipoprotein library (de Kruif et al., *FEBS Lett.,* 399:232–236, 1996, which is incorporated herein by reference); a glycoprotein or glycolipid library (Karaoglu et al., *J. Cell Biol.,* 130:567–577, 1995, which is incorporated herein by reference); or a chemical library containing, for example, drugs or other pharmaceutical agents (Gordon et al., *J. Med. Chem.,* 37:1385–1401, 1994; Ecker and Crooke, *Bio/Technology,* 13:351–360, 1995; each of which is incorporated herein by reference). Accordingly, the present invention also provides a therapeutic agent identified by such a method, for example, a neuroactive therapeutic agent.

The route of administration of a candidate agent will depend, in part, on the chemical structure of the candidate agent. Peptides and polynucleotides, for example, are not particularly useful when administered orally because they can be degraded in the digestive tract. However, methods for chemically modifying peptides, for example, to render them less susceptible to degradation by endogenous proteases or more absorbable through the alimentary tract are well known (see, for example, Blondelle et al., *Trends Anal. Chem.* 14:83–92, 1995; Ecker and Crooke, *Bio/Technology,* 13:351–360, 1995; each of which is incorporated herein by reference). In addition, a peptide agent can be prepared using D-amino acids, or can contain one or more domains based on peptidomimetics, which are organic molecules that mimic the structure of peptide domain; or based on a peptoid such as a vinylogous peptoid.

A candidate agent can be administered to an individual by various routes including, for example, orally or parenterally, such as intravenously, intramuscularly, subcutaneously, intraorbitally, intracapsularly, intraperitoneally, intrarectally, intracisternally or by passive or facilitated absorption through the skin using, for example, a skin patch or transdermal iontophoresis, respectively. Furthermore, the candidate agent can be administered by injection, intubation, orally or topically, the latter of which can be passive, for example, by direct application of an ointment, or active, for example, using a nasal spray or inhalant, in which case one component of the composition is an appropriate propellant.

The total amount of a candidate agent to be administered in practicing a method of the invention can be administered to a subject as a single dose, either as a bolus or by infusion over a relatively short period of time, or can be administered using a fractionated treatment protocol, in which multiple doses are administered over a prolonged period of time. The candidate agent can be formulated for oral formulation, such as a tablet, or a solution or suspension form; or can comprise an admixture with an organic or inorganic carrier or excipient suitable for enteral or parenteral applications, and can be compounded, for example, with the usual non-toxic, pharmaceutically acceptable carriers for tablets, pellets, capsules, suppositories, solutions, emulsions, suspensions, or other form suitable for use. The carriers, in addition to those disclosed above, can include glucose, lactose, mannose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening or coloring agents and perfumes can be used, for example a stabilizing dry agent such as triulose (see, for example, U.S. Pat. No. 5,314,695).

Also provided by the invention is a method of screening for biologically active agents that modulate nicotine hypersensitivity. The method comprises administering a candidate agent to a transgenic animal and determining the effect of the agent upon a phenomenon associated with nicotinic hypersensitivity compared to an effect of the agent administered to a nontransgenic animal. A phenomenon associated with nicotinic hypersensitivity is dopaminergic neuronal cell loss. Methods to asses loss of dopaminergic neuronal cells are known in the art, and include immunohistochemical and anatomical methods, and methods described in Example 2.

The invention will now be described in greater detail by reference to the following non-limiting examples.

EXAMPLE 1

Knock-In Mouse Construction

Xenopus Oocyte Injections and Electrophysiology The α4 and β2 subunits were subcloned into pAMV-PA (Nowak, et al.(1998) Methods Enzymol. 293, 504–529). Capped mRNA transcripts were prepared, and α4/β2 (2 ng, 1:1) or α4L9'/β2 (0.2–0.5 ng, 1:1) were microinjected into Xenopus oocytes. Twenty-four to seventy-two hours later, two-electrode voltage clamp recordings were made in solutions containing zero $Ca^+$.

Figure 1A:
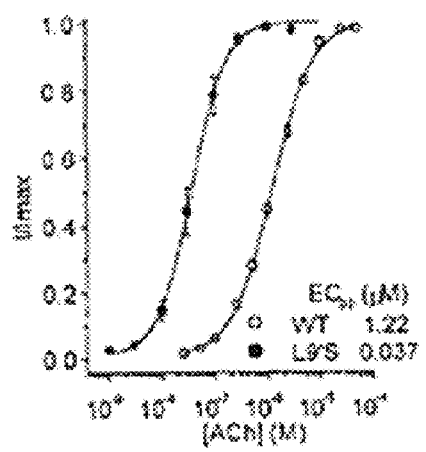
FIGS. 1A–C show the agonist concentration-response relations of WT and mutated (α4 Leu9'Ser) rat α4β2 receptors expressed in oocytes (five oocytes for each curve).
Figure 1B:
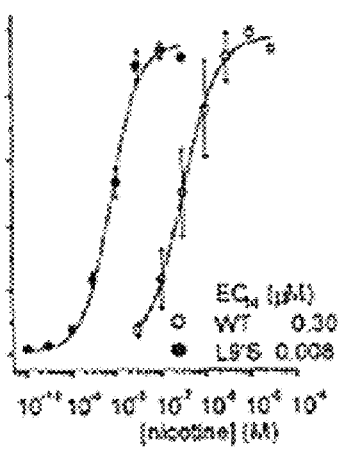
Figure 1C:
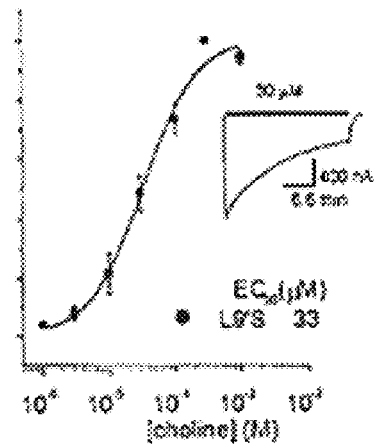
Figure 1D:
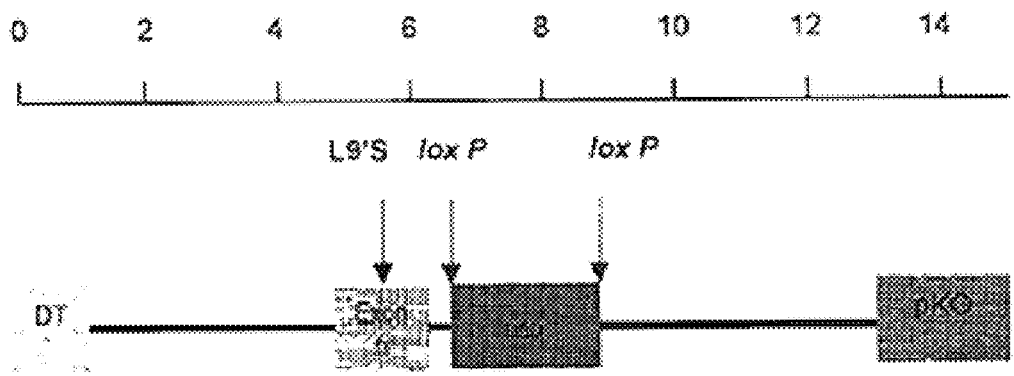
FIG. 1D shows the targeting construct containing exon 5 with the Leu9'Ser mutation, the neomycin resistance gene (neo) flanked by loxP sites, the diphtheria toxin A chain gene (DT), and the pKO V907 vector (pKO).

Knock-in Mouse Construction A 129/SvJ α4 genomic clone containing exon 5 and the L9'S mutation was inserted into pKO Scrambler V907 (Lexicon-Genetics, The Woodlands, Tex.). A neomycin resistance cassette, with a phosphoglycerate kinase promoter and polyadenylation signal and flanked by loxp sites, was inserted 163 bp downstream from exon 5 for positive selection. The diphtheria toxin A chain gene with the RNA polymerase II promoter was inserted to provide negative selection for random insertion. Embryonic stem (ES) cells were electroporated with the linearized construct and screened by Southern blot; the wild-type (WT) gene contains a 9.7-kb, BamFH-BamHI fragment, and the mutant gene contains a 7.7-kb, BanHI-EcoRI fragment (FIG. 1D). The loxP-flanked neomycin resistance cassette was deleted in some ES cells by transfection with a cytomegalovirus-Cre plasmid; this deletion leaves only the 34 bp of one loxP site in the intron. Two lines of mice were generated by injection of mutated ES cells into C57BL/6 blastocysts, one with the neo cassette still present (neo intact) and another with the neo cassette deleted (neo deleted). The presence of the mutation was confirmed by sequence analysis of PCR-amplified gene segments.

Physiological Design and Recombinant Generation of Mutant Genotypes Extending previous studies with the neuronal homomeric α7 and muscle nAChRs (Revah, et at (1991) Nature (London) 353, 846–849; Labarca et al. (1995) Nature (London) 376, 514–516; and Filatov, et al. (1995) Mol. Pharmacol. 48, 379–384), it was determined that the Leu-9'-Ser mutation in the α4 subunit (VTLCISVLLSLTVFLLLIT; SEQ ID NO:1) shifts the dose-response relation for acetylcholine and nicotine about 30-fold to the left for the α4 β2 receptor tested in oocytes (FIGS. 1A and B). The mutated receptor also is activated to 20% of maximal values by choline at a concentration (about 10 μM) that is detected in plasma and cerebrospinal fluid (FIG. 1C) (Klein, et al. (1993) Neurochem. Int. 22, 293–300). Also noted in the present study were increased 8-(diethylamino)octyl 3,4,5-trimethoxyben-zoate hydrochloride (500 nM, nine oocytes) blockable leakage currents in some oocytes expressing the α4L9'S/β2 receptor (Zhong, et al. (1998) Proc. Natl. Acad. Sci. USA 95, 12088–12093), and this may arise from constitutive activation of 1–2% of the receptors; that is, channels open even in the absence of agonist (Bertrand, et al. (1997) NeuroReport 8, 3591–3596). FIG. 1D shows the targeting construct employed in these experiments; FIG. 1E shows the altered region of one α4 allele in 129/SvJ ES cells after homologous recombination and also after Cre recombinase-mediated deletion of the neo selection cassette. Southern blot analysis indicates the presence of the recombinant neo-intact mutant α4 gene in an ES cell line. Similar blots were used then to indicate Cre recombinase-mediated deletion of the neo selection cassette. Chimeric males from the resulting two mouse lines, neo-intact and neo-deleted, were bred to C57BL/6 females to generate animals heterozygous for the mutation, and mice were tested for the mutation by sequencing of genomic DNA (FIG. 1F). Heterozygous animals from the neo-deleted line do not feed and die within 24 hours after birth; a breeding colony bearing this dominant neonatal fatal gene could not be established.

Heterozygous mice from the neo-intact line are viable and fertile, and a breeding colony has been established. (As used hereinafter, use of "heterozygous" refers to this neo-intact line.) Homozygous mutant animals from the neo-intact line do not feed and die within the first postnatal day. The effect of the Leu-9' Ser mutation is probably reduced in heterozygous neo-intact mice because (i) the extent of hypersensitivity, quantified by the reduction in EC50, is expected to increase with the proportion of mutated to normal α4 subunits in the pentameric α4β2 complex; and, (ii) using Western blot analysis, it is found that 3-month-old heterozygous mice express somewhat lower levels of α4 receptors than do WT littermates, in agreement with previous studies on knock-in animals showing that the neo cassette often results in reduced production of the mutated protein (Single, et al. (2000) J. Neurosci. 20, 2558–2566).

Mice were generated expressing a hypersensitive α4 receptor by mutating a single amino acid in the M2 region. This hypersensitivity results in a severe phenotype: perinatal death of animals that carry either a single copy of the dominant neo-deleted allele or two copies of the neo-intact mutant allele. The phenotype of the α4 nAChR knock-in mice is more severe than that of α4 or β2, or even of β2yb4 subunit null mutants (Picciotto, M. R., et al. (1997) Biochem. Soc. Trans. 25, 824–829; Zoli, M, et al. (1999) EMBO J. 18,1235–1244, Xu, W., et al. (1999) J. Neurosci. 19, 9298–9305), arguing against the possibility that the lethality arises primarily from enhanced desensitization or inactivation of α4-containing receptors or from autonomic dysfunction. The phenotype is also more severe than that of knock-in mice bearing a hypersensitive mutation of the α7 nicotinic receptor at the 9' position (Orr-Urtreger, A., et al. (2000) J. Neurochem. 74, 2154–2166); the latter mice display recessive lethality of the neo-deleted line as well as cell death in somatosensory cortex.

EXAMPLE 2

Deficits of Doyaminergic Neurons

Midbrain Progenitor Cells Midbrain progenitor cells were harvested, expanded, and differentiated as described (Potter, E. D., et al. (1999) Cell Tissue Res. 296, 235–246), but epidermal growth factor (20 ng/ml) and basic fibroblast growth factor (ng/ml) were used as mitogens in media treated with choline oxidase. Cells were studied in whole-cell patch clamp experiments (Potter, E. D., et al. (1999) Cell Tissue Res. 296, 235–246).

Histology and Immunocytochemistry Embryos were surgically removed from pregnant females. Tails were removed for genotyping. Embryos were fixed by cardiac perfusion (0.1 M PBS and 4% formaldehyde), postfixed for 2 h, dehydrated in 20% sucrose, and cryosectioned (10 μm) in frontal orientation. Staining was performed with antisera for tyrosine hydroxylase (TH) (1:500) (Chemicon) and α4 nAChR (1:500) (Santa Cruz Biotechnology) and fluorescent secondary antibodies (1:500, Alexa 594, Alexa 488; Molecular Probes), respectively. For cell counts, sections were stained with TH-antisera (Pel-Freez; 1:250) for indirect immunohistochemistry according to the Vectastain ABC Elite kit protocol (Vector Laboratories). Diaminobenzidine was used as the chromogen, with nickel enhancement.

Figure 2:
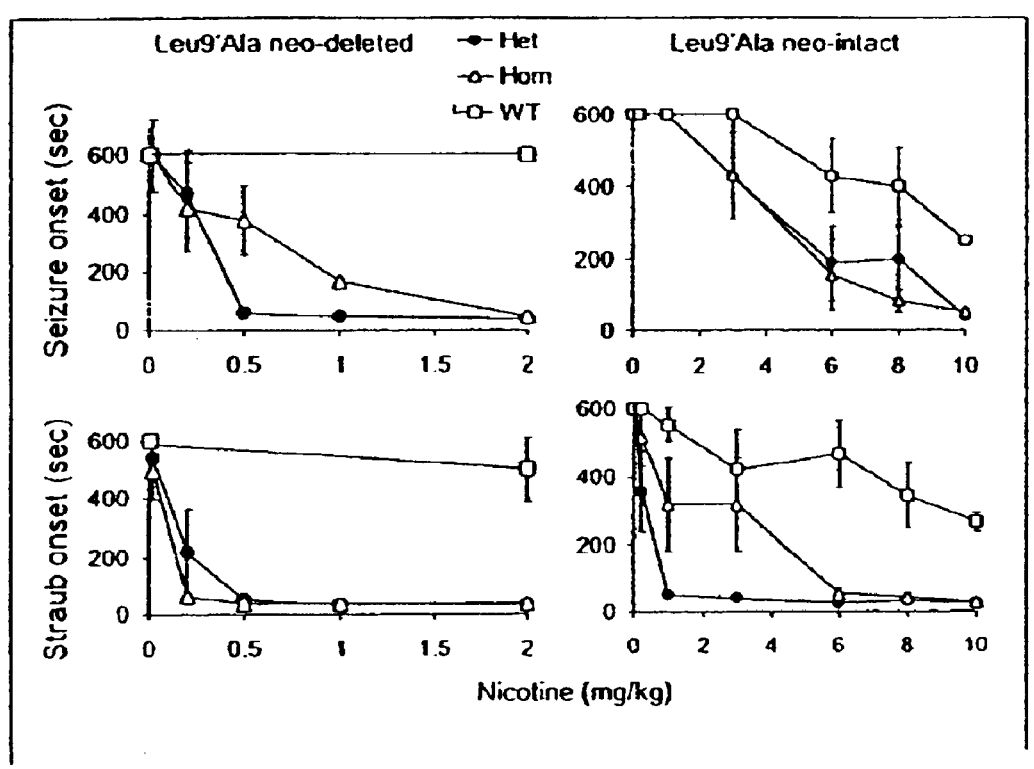
FIG. 2 shows the pathophysiological basis of dopaminergic neuron deficits in mutant mice.

Embryos from matings of heterozygous neo-intact mice (WT, heterozygous, and homozygous for the mutation) and embryos from matings of neo-deleted chimeras with C57BL/6 females (WT and containing one copy of the mutated gene) were collected at embryonic day (ED) 14, 16, and 18. Double immunolabeling with anti-TH and anti-α4 antibodies revealed numerous TH- and α4-immunoreactive cells in the substantia nigra and the ventral tegmental area of WT and heterozygous animals at age ED 14–18. Brains from mutant homozygous embryos of the neo-intact line and from embryos of the dominant lethal neo-deleted line showed normal numbers of immunoreactive cells at ED 14, but a marked reduction in the number of these cells at ED 16 and 18 (FIG. 2C). The severe deficit of nigral dopaminergic cells was the most remarkable anatomical change observed in the brain of the knock-in mouse. Because (α4Leu-9'Ser) β2 mutant receptors expressed in *Xenopus oocytes* are activated by choline at concentrations that occur in plasma and cerebrospinal fluid (FIG. 1C), it is possible that the deficit of dopaminergic neurons in mutant mouse embryos is caused by constant activation of hypersensitive nAChRs on these neurons. To test whether dopaminergic neurons in heterozygous mutant mice are activated by choline, midbrain neuronal progenitor cells were isolated at ED 14–16, differentiated, and responses to applied choline were observed (100 μM). There were choline-induced inward currents in neuron-like cells derived from heterozygous mice, but much smaller currents in those derived from WT animals (FIGS. 2B and C), ruling out a major contribution from endogenous α7 nicotinic receptors (Charpantier, et al. (1998) *NeuroReport* 9, 3097–3101). In cells from homozygous neo-intact mice, the responses to choline were so large that recordings were lost after the first application.

The brain of mutant embryos showed no gross abnormalities. Substantia nigra dopaminergic neurons were specifically investigated in this study, both because these cells express high densities of α4-containing receptors (Arroyo-Jimenez, M. Det al. (1999) *J. Neurosci.* 19, 6475–6487) and because NURRI knock-out mice, which specifically lack these neurons, also die shortly after birth (Zetterstrom, R., et al. (1997) *Science* 276, 248–250). Some mutant nAChRs that cause human slow-channel congenital myasthenic syndrome are activated by serum levels of choline, and this continuous channel activity is thought to contribute to the pathophysiology of the disease (Zhou, M., et al. (1999) *Proc. Natl. Acad. Sci. USA* 96, 10466–10471). The evidence presented herein shows that continuous activation by choline is a likely mechanism underlying the deficit of dopaminergic neurons. Previous data also establish that chronic stimulation of nicotinic receptors in the brain produces developmental anomalies, including extensive cytotoxicity and premature withdrawal from the cell cycle (Berger, F., et al. (1998) *J. Neurosci.* 18, 6871–6881). Detailed studies of other brain regions that express α4 receptors have yet to be completed. Knock-in animals with gain of function mutations in nicotinic receptors are useful models for neurodegenerative diseases.

EXAMPLE 3

Characterization of Heterozygote Motor Activity

Ambulation (FIGS. 3A, B, D, and E) was measured in Pasadena, Calif. Single events represented disruption of two distinct light beams 10 cm apart in the cage (San Diego Instruments). Nicotine (0.02 mg/kg nicotine equivalent of nicotine hydrogen tartrate salt dissolved in 0.9% saline) or amphetamine (5 mg/kg d-amphetamine sulfate dissolved in 0.9% saline) was injected i.p. in a volume of 100–200 μl (100 μl/20 g body weight). Mice were shipped to Boulder, Colo. and acclimated for 21 days before testing by personnel blind to the genotype at 110–133 days of age (22 each WT mice and mutant littermates). Week 1 involved baseline anxiety, measured in the elevated plus maze (Lister, R. G. (1987) *Psychopharmacology* 92, 180–185; Bowers, B., et al. (2000) *Behav. Genet.* 30, 111–121), followed by mirrored chamber (Toubas, P. L., et al. (1990) *Pharmacol. Biochem. Behav.* 35, 121–126; and Lister, supra) and light/dark box (Lister, supra, and Crawley, J. et al. (1980) *Pharmacol. Biochem. Behav.* 13, 167–170). Week 2 involved startle and prepulse inhibition of startle, then 3 days on the accelerating rotarod (Ugo Basile, Varese, Italy), at speeds increasing gradually from 4 to 40 rpm over 500 s. In week 3, contextual and cued fear conditioning was as described (Young, E. A, et al. (2000) *Brain Res.* 860, 95–103), except that a 0.7-mA shock was used for fear conditioning. A separate group of mice derived from the first backcross onto C57BL/6J mice also were tested for gross ataxia on a circular mesh (0.5 3 0.5 cm squares) elevated 23 cm from a plastic square arena. All behavioral data were analyzed with ANOVA procedures and SPSS Version 9 software.

There were no gross physical differences between heterozygotes and WT littermates of both sexes from the neo-intact line. The genotypes did not differ in weight, and all exhibited normal grooming behavior and social interactions with cage mates. There was no significant effect of genotype on any measure of fear conditioning. Nonetheless, detailed characterization revealed a specific pattern of behavioral differences between the heterozygotes and WT mice.

Figure 3E:
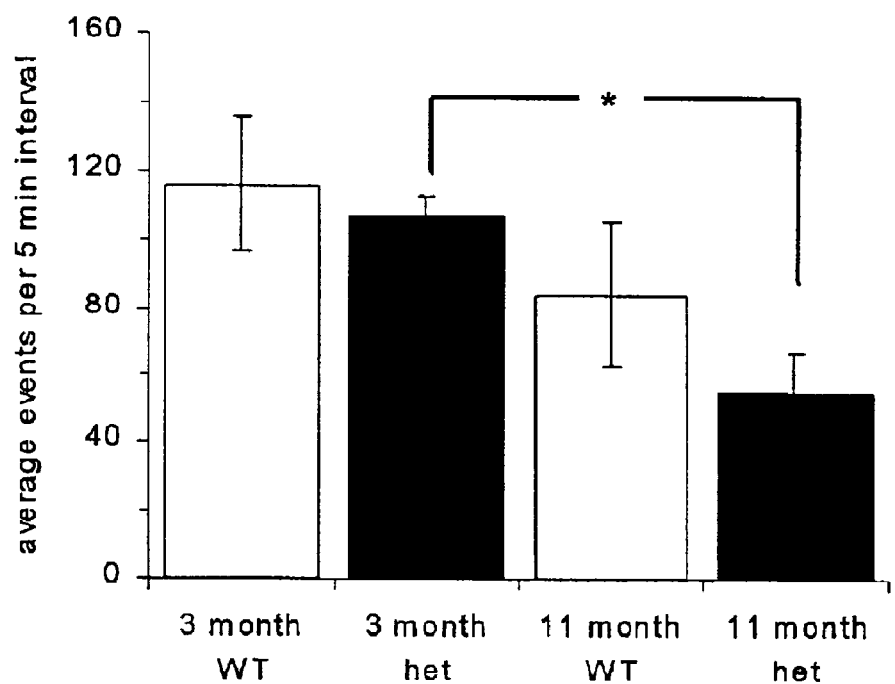

When mice are placed in the test cage, they explore the new surroundings and show a transiently increased level of ambulation for about 30 min (FIG. 3A). During this period, the knock-in mice show a significantly higher level of ambulation than the WT controls. The genotype X time interaction was characterized by [F(1,17) 5 5.2; P, 0.001]. Whereas WT mice are not affected by an administration of 0.02 mg/kg of nicotine, this treatment sharply reduces the level of activity of the knock-in mice [group X time interaction=F(1,14)=1.89; P, 0.05] (FIG. 3B). Concentrations of nicotine that affect behavior of unhabituated WT mice are 10- to 100-fold higher.

In the accelerating rotarod test, the α4 heterozygotes also exhibited abnormalities in a measure of motor learning (FIG. 3C). Heterozygotes and WTs performed equally on the first day of testing. Both genotypes showed some improvement across days in their ability to remain on the accelerating rotarod [F(2,80)=30.2; P, 0.001], but heterozygotes performed more poorly overall on later days [F(1,40)=6.91; P, 0.012]. Because there is little α4 expression in the cerebellum and no gross ataxia was detected in the cα4 heterozygotes (all six heterozygous and all 10 WT mice remained on the mesh for the entire 5-min test period), it is likely that cerebellar function is normal in the α4 heterozygotes. Thus the impairment of motor coordination is most likely another correlate of dysfunction of dopaminergic neurons (albeit to a lesser extent than the fatal cell loss in either the homozygous neo-intact animals or in neo-deleted animals carrying even a single copy of the mutant gene). The hypersensitive α4 allele did not produce an overall change in reactivity as measured by acoustic startle response, prepulse inhibition, contextual learning, or auditory cued conditioning. Locomotor responses to amphetamine were examined as a behavioral measure of nigrostriatal function. Intraperitoneal injection of 5 mg/kg amphetamine stimulated locomotion in young (about 3-month-old) mice, and there was no significant difference between WT mice and their heterozygous littermates. When the same group of animals was tested at 11 months of age, there was reduced amphetamine-induced locomotion in heterozygous but not in WT mice (FIGS. 3D and E). It is likely that the reduction of the amphetamine response in older heterozygous mice is due to accelerated loss of function in their dopaminergic neurons.

Increased Anxiety of Heterozygous Knock-In Mice Heterozygotes were significantly more anxious than WT mice (FIG. 4). In the elevated plus maze (FIG. 4A), heterozygotes displayed more anxiety as measured by percentage of entrances into open arm [$F(1,44)=7.35$; P, 0.01], percentage of time in open arms [$F(1,44)=10.8$; P, 0.002], percentage of time in the closed arms [$F(1,44)=6.64$; P, 0.02], and the number of times to the end of the open arm [$F(1,44)=8.6$; P, 0.005]. There was no effect of genotype on percentage of time in the center [$F(1,44)=1.82$; not significant] or number of total entries into all arms [$F(1,44)=1.29$; not significant].

There was no overall difference in activity in this maze, as evidenced by a lack of difference in the total entries in all arms and time spent in the center of the maze. These measures are consistent with overall greater anxiety in the heterozygotes.

In another measure of anxiety, the mirrored chamber test (FIG. 4B), heterozygotes displayed more anxiety as measured by: latency (seconds) to enter mirrored chamber [$F(1,44)=5.9$; P<0.019] and number of entrances into the mirrored chamber [$F(1,44)=5.9$; P<0.014]. There was no difference in times walking through the mirrored passage [$F(1,44)=2.2$; not significant].

In a third test of anxiety, the light/dark box, heterozygotes did not differ from WTs on the following measures: total transitions (15.1±1.7 vs. 17.3±0.9); percentage of time in the light box (34.6±2.8 vs. 31.0±1.3); latency to enter the dark side (17.6±2.7 vs. 12.6±1.9). This lack of difference in the light/dark box compared with increased anxiety measured in other mazes has been observed previously in a corticotropin-releasing hormone receptor-2 null mutant mouse (Bale, T. L et al. (2000) *Nat. Genet.* 24, 410–414). Anxiety is a multidimensional behavior, and each test may evaluate only a subset of these dimensions.

The results described herein with the viable neo-intact heterozygous α4 knock-in mice support a role for α4-containing receptors in the control of baseline anxiety. Nicotine is known to reduce anxiety or to produce a bimodal effect on anxiety (File, S. E., et al. (1998) *Behav. Neurosci.* 112, 1423–1429). Nicotinic receptors modulate the release of neurotransmitters that have critical roles in the regulation of anxiety (gamma-aminobutyric acid, dopaamine, and serotonin) (O'Neill, A. B. et al. (1994) *Pharmacol. Biochem. Behav.* 49, 755–757), and it will be important to investigate the hypothesis that these mice have reduced gamma-aminobutyric acid release. Functional changes due to the hypersensitive nicotinic receptors on dopaminergic neurons in the α4 heterozygotes could also contribute at least in part to increased anxiety. (Increased anxiety is often associated with Parkinson's disease.) Consistent with this possibility, treatment with D2 but not D1 dopamine receptor antagonists increases anxiety in rodents (Timothy, C et al. (1999) *Pharmacol. Biochem. Behav.* 62, 323–327). Finally, locomotion of the heterozygous knock-in mice is extremely sensitive to nicotine, suggesting that these mice may also become a model for effects of nicotine on mammalian brain and behavior.

EXAMPLE 4

Seizure Activity and Autosomal Dominant Nocturnal Frontal Lobe Epilepsy

Behavioral and electroencephalographic data show that transgenic mice haivng a L9'S mutation in the α4 subunit have a 5- to 10-fold increase in sensitivity to nicotine-induced seizures when compared to wild type littermates.

Electrophysiological studies on brain slices derived from transgenic α4 mice. Slices obtained from frontal cerebral cortex, hippocampus, and midbrain can be used for field and intracellular recordings. Field recordings serve to determine whether various compounds cause or block synchronized firing in these neuronal ensembles. Whole-cell patch recordings provide information regarding activation and/or desensitization of nAChRs in individual neurons when exposed to various agonists and antagonists, as well as the effects of these compounds on firing rates. Because interneurons express most of the α4 receptors, recordings from interneurons and IPSC's in pyramidal cells are useful for study. Experiments with acute midbrain slices have shown that cells from animals heterozygous for the α4 mutant transgene respond to acetylcholine and nicotine at concentrations ten times lower than those that activate receptors in slices from wild type animals. nAChRs agonists and antagonists, such as nicotine, choline, dihydro-β-erythroidine, as well as non-cholinergic neuroleptics, such as bicuculline and kainic acid are likely to induce or block seizures in transgenic α4 mice.

Electrophysiological properties of nAChRs in primary cell cultures derived from the transgenic α4 mice. Primary cell cultures allow the testing of several detailed functional aspects of nicotinic function. Synaptic physiology, with specific emphasis on nicotinic effects on inhibitory interneurons and on transmitter release from presynaptic can be examined. In these experiments, an additional mouse mutant line whose GABAergic intemeurons fluoresce because they express a GFP-tagged GABA transporter will be used. Therefore, electrophysiological properties can be matched to neuronal cell type, providing useful information to identify cells responsible for seizure initiation. Electrophysiological studies with fara-2 measurements of Ca influx, and with cell labeling techniques can also be performed.

Figure 5:
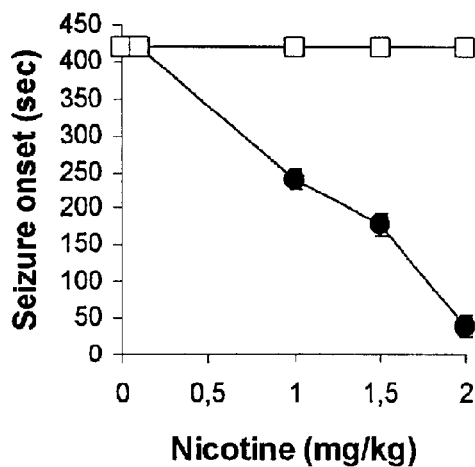
FIG. 5 shows behavioral scoring of seizure activity in heterozygous and wild type mice following subcutaneous nicotine injection.
Figure 5:
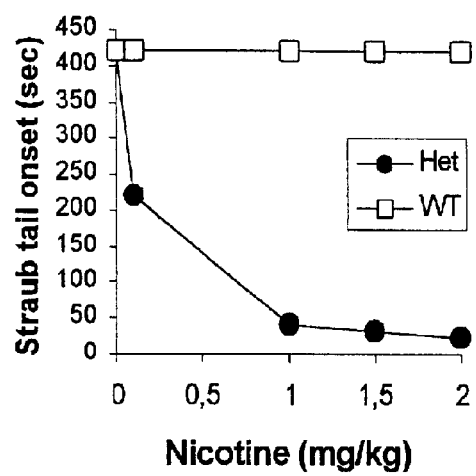

To pharmacologically characterize the L9'S mutation effects on seizure induction in the α4 mice behavioral responses to pharmacologic stimulation were videotaped and scored. Transgenic animals heterozygous (hets) for the L9'S mutation, but not wild-types (WT), displayed Straub tail (90° lifting of tail) and seizures with a dose dependent decrease in latency at nicotine doses ranging from 1 mg/kg to 2 mg/kg (s.c.) (see FIG. 5). WT animals required higher doses of nicotine (>10 mg/kg) in order to display the severe tonic-clonic seizures observed in hets. In addition, hets exhibited less variability in their behavioral patterns consisting of Straub tail, seizures, circling and head swaying compared to WT. The specific nicotine binding site blocker mecamylamine (2 mg/kg), partially blocked nicotine effects in both hets and WT.

Mouse electroencephalography can also be used to examine the susceptibility of transgenic mice to seizures. A surgical and electrophysiological rig that allows simultaneous video-electroencephalographic (EEG) recordings in free moving animals can be used. For EEG electrode implants, mice are anesthetized with a ketamine-xylazine mixture, 0.2 mm-diameter tungsten wire electrodes are positioned through drilled holes in the cranium in a twisted pair configuration and placed stereotactically within different regions of the brain. A three-pin microconnector (ground electrode plus two recording electrodes) is cemented to the skull surface. Following surgery, mice are allowed to recover for 48 hours. Rapid-burst discharges in a heterozygous mouse following nicotine injection (0.1 mg/kg) was observed accompanied by a two-fold increased amplitude of 6 Hz theta rhythm, and stereotyped behaviors such head bobbing and circling. EEG recordings of WT were unaffected by nicotine (0.1 mg/kg). These data underscore the importance of the α4 subunit of nAChRs during nicotine-induced seizures.

To further examine seizure-induction sensitivity of the α4 mutated mice, the following nicotinic agonists will be tested in their ability to cause seizures: 1) ACh is the endogenous agonist of nAChRs and heterologous expression of the L9'S mutation resulted in a 30 fold increase in ACh sensitivity. 2) Choline; although very low concentrations of this agonist circulate in the CNS, ACh degradation by cholinesterase may render higher local synaptic concentrations of choline that could activate mutated nAChRs (Labarca, et al. (1995) Nature 376, 514–516) Cytisine may help discriminate between the α4β2 and α7 nAChRs as it is considered a weak agonist of the former but a full agonist of the latter. A number of nicotinic receptor antagonists can be surveyed for their ability to block or induce seizures in transgenic α4 mice. For example, mecamylamine is a non-competitive nicotinic antagonist that targets most nAChRs, and has been reported as an effective nicotine-induced seizure blocker (Damaj, et al. (1999) J Pharmacol Exp Ther 289, 1229–36). Dihydro-β-erythroidine (DHOE) is a competitive nicotinic antagonist with high selectivity for α4β2 receptors. Interestingly, DHβE has been reported to induce seizures in rats, supporting the hypothesis that a loss of function or increased desensitization of α4β2 receptors could result in a decrease in GABA release and cause convulsions by excessive desinhibition (Felix and Levin (1997) Neuroscience 81, 1009–17). Methyllycaconitine citrate (MLA) is an antagonist with high selectivity for α7 homomeric receptors.

Two convulsants can be used to test the null hypothesis that transgenic α4 animals and WT will not differ in their sensitivity to non-cholinergic seizure-inducing compounds. Such convulsants include bicuculline, \a $GABA_A$ receptor blocker known to induce seizures in rodents by reducing inhibition and kainic acid (KA), a kainate glutamate receptor agonist, widely used as an experimental model for temporal lobe epilepsy. Bicuculline and KA can act down-stream from the action of nAChRs, and thus the transgenic and the WT animals can have similar seizure characteristics, such as latency and dose dependence. However, it should not be surprising, if these neuroleptics summate to the L9'S mutation effect, indicating that mutant animals are closer to seizure threshold compared to WT.

Stereotactic electrode placement can determine where seizures originate. The cortex and the hippocampus can be tested and EEG patterns can be analyzed for onset and intensity of interictal spikes. Also, the substantia nigra-thalamic axis can be examined because it contains a high density of nAChRs and is considered a pathway that gates and controls seizure propagation. The animals can be videotaped for 24 hour cycles to determine if spontaneous seizures occur.

Brain slices can used to examine synaptic transmission in the L9'S transgenic mouse. In general, it is believed that most types of epilepsy, including ADNFLE, involve neocortical and hippocampal circuits (Noebels, J. L. (1996). Neuron 16, 241–4). ADNFLE mutations have been reported to modify nAChRs activity when expressed in heterologous systems. Such changes may alter excitatory or inhibitory synaptic transmission, eventually leading to seizure induction. In the hippocampus for example, inhibitory interneurons expressing α4β2 receptors, synapse onto glutamatergic pyramidal cells. Activation of mutated nAChRs on GABAergic synaptic terminals may decreases GABA release, leading to decreased inhibition of pyramidal cells. The effects of nicotinic agonists and antagonists on the GABAergic input to pyramidal cells can be examined.

To compare the strength of GABAergic inhibition in brain slices from transgenic L9'S and WT mice, several experimental approaches can be used. First, hippocampal slices, cut 300 μm thick, using a Dosaka (Japan) vibratome can be used. A primary purpose of inhibition is to prevent the generation of action potentials. A way to assess action potential generation is to measure the amplitude of the population spike in stratum pyramidale of area CA1 of the hippocampus in response to stimulation of the Schaffer collaterals. The effect of inhibition on action potential generation may be measured using paired-pulse stimulation. This technique has been used effectively to study seizures in other epileptic mouse models such as the neuropeptide Y knock-out mouse (Baraban, et al (1997). J. Neurosci 17, 8927–36). Extracellular electrodes are placed to stimulate and record from presynaptic and postsynaptic areas respectively. Low-intensity stimuli to the Schaffer collaterals produces EPSC's; high intensities produce population spikes. If two stimuli are applied 50 ms apart, inhibition activated by the first stimulus reduces EPSC's and population spikes in response to the second. The effect of inhibition on action potential generation can be quantified by comparing the amplitude in the absence and presence of an antagonist of the GABAAreceptor such as bicuculline (30 μM) or picrotoxin (50 μM). It is likely that blocking GABAA receptors will have a smaller effect on paired-pulse facilitation in transgenic L9'S than in wild-type. Paired-pulse facilitation can also be used to estimate $Ca^{2+}$ influx to the presynaptic terminal. The principle is that with each stimulus, $Ca^{2+}$ enters the presynaptic terminal, and left over $Ca^{2+}$ from the first pulse, potentiates neurotransmitter release and thus the postsynaptic response following the second pulse. Because changes in presynaptic terminal [$Ca^{2+}$] are proportional to changes in neurotransmitter release, paired-pulse facilitation will serve to determine presynaptic calcium concentration fluctuations. Paired-pulse facilitation can therefore determine whether, and to what extent, changes in $Ca^{2+}$ permeability due to the L9'S mutation affect presynaptic activity.

Another way to assess the strength of inhibition is to measure the size and frequency of spontaneous inhibitory events. Whole-cell patch clamp recordings from CA1 pyramidal cells under visual control using infrared differential interference contrast (IR-DIC) imaging can be used. Cells can be viewed during recordings using an Olympus upright microscope model BX50WI outfitted with IR-DIC. By using an internal solution with a [$Cl^-$] and including the glutamate receptor antagonists CNQX and APV in the bath, miniature IPSCs can be recorded. It is likely that the miniIPSCs are smaller and less frequent in transgenic L9'S animals than in wild-type animals. During the recordings, exposure to nicotinic agonists and antagonists can be included to see the effect of nAChRs desensitization on spontaneous release. Bathing solution in all experiments contain atropine to block muscarinic receptors.

The strength of unitary synaptic connections can be compared by simultaneously recording from an inhibitory interneuron and a pyramidal cell onto which it synapses. In addition to visual identification, the firing pattern in response to depolarizing current injections can be assessed to increase confidence in their identities as interneurons. There is a reasonable probability of finding synaptically connected pairs because each inhibitory interneuron synapses onto a large number of pyramidal cells. This method allows a comparison of the baseline strength of inhibitory synaptic connections between L9'S transgenic animals and WT animals, and how these synapses are modulated by nicotinic agonists and antagonists. Dual simultaneous recordings allow activation/desensitization events to be directly correlated with postsynaptic excitation/inhibition events. Enhanced desensitization in inhibitory presynaptic interneurons of L9'S transgenic animals compared to WT animals results in either smaller IPSC's or EPSC's in postsynaptic pyramidal cells.

The paradigms described above can be implemented in slices derived from other brain areas such as the cortex and the midbrain. Large inhibitory and excitatory potentials can be recorded from pyramidal cells in cortical slices (Hasselmo and Barkai (1995). *J. Neurosci* 15, 6592–604). Experiments showed that a majority of neurons from transgenic mice responded with spontaneous bursts to 10 μM nicotine, while the WT-derived cells remained silent or required much larger concentrations to be activated. This result confirms the expression of mutant AChRs in L9'S mice and its gain of function phenotype.

Cortical and hippocampal primary cell cultures derived from E18 or P1–3 L9'Stransgenics and WT embryos (Nadeau, et al. (2000) *J. Neurophysiol.* 84, 1062–75.). Synaptic physiology, emphasizing nicotinic effects on inhibitory interneurons and on transmitter release from presynaptic terminals can be examined. Embryos derived from the cross between transgenic L9'S mice and GFP-tagged GABA transporter mice can provide cultures in which GABAergic neurons are labeled with green fluorescence. This cell labeling strategy simplifies the task of identifying GABAergic inhibitory neurons versus excitatory ones during electrophysiology experiments. A puffer pipette located near the cell body can deliver ACh, nicotine or other nicotinic ligands. A piezoelectric double-barrel system that allows one to alternate between barrels quickly can be used. The purpose of the piezoelectric pipette is to have precise control of drug delivery so that nAChRs desensitization by passive diffusion is avoided. IPSC's or EPSC's recordings can be complemented with presynaptic recordings to assess whether, cholinergic ligands' effects on nAChRs, such as activation or desensitization, cause excitatory or inhibitory synaptic transmission.

Fura-2 ratiometric measurements can also be mad using a video imaging system equipped with an inverted microscope (Olympus IMT2, modified for 340 nm) and a Photometrix Quantix CCD camera running Axon Imaging Workbench 4.0. A Sutter filter wheel provides alternate 340 nm and 380 nm illumination. A Bioptechs recording chamber allows for perfusion and heating, when necessary. Changes in calcium concentration are estimated by calculating the 340/380 ratio. Ratiometric measurements on various cells in culture can be perfomed while perfusing or pressure injecting nicotinic ligands. Fura-2 recordings directed at specific cell types, can assess $Ca^{2+}$ permeability changes due to the introduction of the L9'S mutation. GABAergic interneurons can be identified as described herein, or a-posteriori with inmunocytochemistry, and then $Ca^{2+}$ fluctuations can be assessed during nAChRs stimulation with ACh, nicotine and other ligands. It is likely that $Ca^{2+}$ levels increase less in L9'S GABAergic interneurons than in WT cells upon nicotinic stimulation.

Results from several studies on α4 transgenic animals reveal the following results. (a) L9'S transgenic nAChRs expressed in frog oocytes have increased sensitivity to ACh, nicotine and choline, meaning that smaller concentrations of these ligands tend to activate these receptors and allow depolarizing currents and $Ca^{2+}$ in. (b) L9'S mutated knock-in mice have a reduced threshold to nicotine-induced seizures. (c) In addition, it is thought that nAChRs' main role in the brain is to modulate presynaptic inhibitory interneurons' neurotransmitter release. Thus, ACh or nicotine administration to the mutant mice is likely to result in enhanced GABA release and subsequent inhibition of pyramidal cells in the cortex, the hippocampus and probably elsewhere in the brain. These results may indicate that seizure is more likely, however, other factors and characteristics must be considered. For example, nicotine induces increased desensitization of mutated nAChRs resulting in less GABA release. (b) Although there may be initial activation of nAChRs, recurrent loops within interneurons expressing nAChRs, may cause the inhibition of GABAergic terminals that synapse onto excitatory neurons. (3) Postsynaptic mutated nAChRs play an important role in excitatory transmission. (4) Developmental changes due to the mutated nAChRs have resulted in altered circuitry that nullifies presupposition c.

Although the invention has been described with reference to the above examples, it will be understood that modifications and variations are encompassed within the spirit and scope of the invention. Accordingly, the invention is limited only by the following claims.

What is claimed is:

1. A heterozygous transgenic knock-in mouse comprising a transgene encoding a leucine-to-serine mutation or a leucine-to-alanine at position 9' in the M2 transmembrane region of the α4 nicotinic receptor subunit, wherein the transgene is introduced into the endogenous gene by homologous recombination, and wherein the expression of the mutant receptor subunit gene results in a mouse that displays modified behavior compared to a normal mouse.

2. The heterozygous transgenic knock-in mouse of claim 1, wherein the mouse displays nicotinic hypersensitivity, increased anxiety, poor motor learning, excessive ambulation, displays a reduction in dopaminergic neuron function upon aging, susceptibility to seizure, spontaneous seizure, or any combination thereof.

3. A method for producing a heterozygous transgenic knock-in mouse having a modified behavior compared to a normal mouse, comprising (a) introducing a transgene comprising a selectable marker sequence and encoding a leucine-to-serine mutation or a leucine-to-alanine mutation at position 9' in the M2 transmembrane region of an α4 nicotinic acid receptor subunit into a mouse embryonic stem cell; (b) selecting a mouse ES cell which has undergone homologous recombination with the transgene; (c) introducing said mouse embryonic stem cell which contains the transgene into a mouse embryo; (d) transplanting said embryo into a pseudopregnant mouse; (e) allowing said embryo to develop to term, thereby obtaining a chimeric mouse containing said transgene in its genome, and (f) mating said chimeric mouse with a normal mouse, which lacks the transgene, thereby obtaining a heterozygous transgenic knock-in mouse whose genome comprises a transgene encoding a leucine-to-serine mutation or a leucine-to-alanine mutation at position 9, in the M2 transmembrane region of the endogenous α4 nicotinic receptor subunit gene, said heterozygous transgenic knock-in mouse having a modified behavior compared to a normal mouse.

4. A method for screening a candidate agent for the ability to modulate nicotine-mediated behavior in the transgenic knock-in mouse of claim 1, comprising:
   (a) administering to a first heterozygous transgenic knock-in mouse of claim 1 a candidate agent, and
   (b) comparing the nicotine-mediated behavior of the first heterozygous transgenic knock-in mouse to nicotine-mediated behavior of a second heterozygous transgenic knock-in mouse of claim 1 not administered the candidate agent;
   wherein a difference in the modified behavior in the first heterozygous transgenic knock-in mouse administered the candidate agent compared to the second heterozygous transgenic knock-in mouse or the normal mouse not administered the candidate agent is indicative of a candidate agent that modifies nicotine-mediated behavior.

5. A method of screening for candidate agent that modulates nicotine hypersensitivity comprising:
   (a) administering a candidate agent to a heterozygous transgenic knock-in mouse of claim 1;
   (b) determining the effect of the agent upon a cellular or molecular process associated with nicotinic hypersensitivity in the heterozygous transgenic knock-in mouse compared to an effect of the agent administered to a non-transgenic mouse,
   wherein a difference in effect is indicative of an agent that modulates nicotine hypersensitivity.

6. A method of screening for a candidate agent that modulates seizure activity associated with epilepsy, comprising (a) administering a candidate agent to a transgenic knock-in mouse of claim 1;

(b) determining the effect of the agent upon seizure activity associated with epilepsy in the transgenic knock-in mouse compared to an effect of the agent administered to a non-transgenic mouse, wherein a difference in effect is indicative of an agent that modulates seizure activity associated with epilepsy.

7. A transgenic knock-in mouse comprising a transgene encoding a leucine-to-alanine mutation at position 9' in the M2 transmembrane region of the α4 nicotinic receptor subunit, wherein said transgene is introduced into the endogenous gene by homologous recombination, and wherein expression of the mutant receptor subunit gene results in a mouse that displays modified behavior compared to a normal mouse.

8. The transgenic knock-in mouse of claim 7, wherein the knock-in mouse displays nicotinic hypersensitivity, increased anxiety, poor motor learning, excessive ambulation, displays a reduction in dopaminergic neuron function upon aging, susceptibility to seizure, spontaneous seizure, or any combination thereof.

9. A method for screening a candidate agent for the ability to modulate nicotine-mediated behavior in the transgenic knock-in mouse of claim 7, comprising:

(a) administering to a first transgenic knock-in mouse of claim 7 a candidate agent, and (b) comparing the nicotine-mediated behavior of the first transgenic knock-in mouse to nicotine-mediated behavior of a second transgenic knock-in mouse of claim 7 not administered the candidate agent;

wherein a difference in the modified behavior in the first transgenic knock-in mouse administered the candidate agent compared to the second transgenic knock-in mouse or the normal mouse not administered the candidate agent is indicative of a candidate agent that modifies nicotine-mediated behavior.

10. A method of screening for candidate agent that modulates nicotine hypersensitivity comprising:

(a) administering a candidate agent to a transgenic knock-in mouse of claim 7;

(b) determining the effect of the agent upon a cellular or molecular process associated with nicotinic hypersensitivity in the transgenic knock-in mouse compared to an effect of the agent administered to a non-transgenic mouse, wherein a difference in effect is indicative of an agent that modulates nicotine hypersensitivity.

11. A method of screening for a candidate agent that modulates seizure activity associated with epilepsy, comprising (a) administering a candidate agent to a transgenic knock-in mouse of claim 7;

(b) determining the effect of the agent upon seizure activity associated with epilepsy in the transgenic knock-in mouse compared to an effect of the agent administered to a non-transgenic mouse, wherein a difference in effect is indicative of an agent that modulates seizure activity associated with epilepsy.

* * * * *